US00PP31381P2

(12) United States Plant Patent
O'Neill

(10) Patent No.: US PP31,381 P2
(45) Date of Patent: Jan. 21, 2020

(54) ***IXORA* PLANT NAMED 'VISTA6'**

(50) Latin Name: *Ixora taiwanensis*
Varietal Denomination: Vista6

(71) Applicant: Jerome O'Neill, Juana Diaz, PR (US)

(72) Inventor: Jerome O'Neill, Juana Diaz, PR (US)

( * ) Notice: Subject to any disclaimer, the term of this patent is extended or adjusted under 35 U.S.C. 154(b) by 0 days.

(21) Appl. No.: 16/350,579

(22) Filed: Dec. 3, 2018

(51) Int. Cl.
*A01H 5/02* (2018.01)
*A01H 6/76* (2018.01)

(52) U.S. Cl.
USPC ..... Plt./226
CPC ..... *A01H 6/76* (2018.05)

(58) Field of Classification Search
USPC ..... Plt./226
See application file for complete search history.

*Primary Examiner* — Anne Marie Grunberg
(74) *Attorney, Agent, or Firm* — Cassandra Bright

(57) ABSTRACT

A new and distinct cultivar of *Ixora* plant named 'Vista6' is disclosed, characterized by white flowers and large, dark green foliage. Plants are more vigorous than typical for white flowering *Ixora*. The new variety is a *Ixora*, typically produced as an ornamental plant.

1 Drawing Sheet

Latin name of the genus and species: *Ixora taiwanensis*.
Variety denomination: 'Vista6'.

BACKGROUND OF THE INVENTION

The new cultivar is the product of chance discovery. The new variety originated as naturally occurring whole plant mutation of the unpatented variety *Ixora taiwanensis* 'Hawaiian Pink', unpatented. The inventor discovered the variety in a commercial planting of the parent variety in Juana Diaz, Puerto Rico in February of 2016.

After identifying the interesting flower color mutation, the inventor observed the single plant mutation for several months. First propagation was performed by terminal vegetative cuttings at a commercial greenhouse during March of 2016, in Juana Diaz, Puerto Rico. Access to all plants was restricted, as plants were kept in a facility belonging to the inventor and not open to the public. Date of first sale was Jan. 31, 2018. This sale was made directly by the inventor or one who obtained the claimed invention directly or indirectly from the inventor. This sale and all public disclosures made before the filing of this application fall within the exception allowed under 102(b)(1).

Through subsequent propagation by vegetative cuttings, multiple generations have been reproduced, which have shown that the unique features of this cultivar are stable and reproduced true to type.

SUMMARY OF THE INVENTION

The cultivar 'Vista6' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Vista6'. These characteristics in combination distinguish 'Vista6' as a new and distinct *Ixora* cultivar:

1. White flowers.
2. Vigorous plant.
3. Large foliage.

PARENT COMPARISON

Plants of the new cultivar 'Vista6' are similar to the parent, in most horticultural characteristics. The new variety, however, differs in the following:

1. The new variety has white flowers; parent has pink flowers.

COMMERCIAL COMPARISON

Plants of 'Vista6' are similar in some horticultural characteristics to the variety *Ixora taiwanensis* 'Dwarf White', unpatented. The new variety, however, differs in the following:

1. The new variety has larger leaves than the comparator.
2. Plants of the new variety are more vigorous than plants of the comparator.

Plants of 'Vista6' are similar in most horticultural characteristics to the variety *Ixora taiwanensis* 'Pink', unpatented. The new variety, however, differs in the following:

1. New variety has white flowers; comparator has pink flowers.

BRIEF DESCRIPTION OF THE PHOTOGRAPH

The accompanying photograph illustrates in full color a typical plant of 'Vista6' grown outdoors at a commercial nursery in Juana Diaz, Puerto Rico. This plant is approximately 6 months old, shown in a five inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'Vista6' plant. This plant was grown in a greenhouse in a commercial 6 inch pot, in Juana Diaz, Puerto Rico. The plant described is approximately 6 months old and consists of 3 rooted cuttings in 1 pot. Temperatures ranged from 15° C. at night and 18° C. to 24° C. during the day. No artificial light, photoperiodic treatments were given to the plants. Measurements and numerical values represent averages of typical plant types.

Botanical classification: *Ixora taiwanensis* 'Vista6'.

PROPAGATION

Time to initiate roots: About 30 days at approximately 25° C.

Root description: Roots are moderately dense, well branched, semi-woody.

Time to produce a rooted plant: Approximately 6 to 12 weeks.

Root color: Near RHS Grey-Brown 199D.

PLANT

Growth habit: This plant is an upright tender perennial, suitable for outdoor garden use in warm climates.

Pot size of plant described: 5 inch.

Height: 20 cm.

Plant spread: 20 cm.

Shape: Oval to round.

Main stem color: Near RHS Grey-Brown 199B.

Main stem texture: Very slightly scaly.

Branching characteristics: Not free branching, moderate branching can be achieved with pinching.

Length of primary lateral branches: Average 8 cm.

Quantity of primary lateral branches: 3 per plant.

Characteristics of primary lateral branches:

*Diameter.*—Approximately 3 to 7 mm.

*Color.*—Near RHS Greyed-Green 191A.

*Texture.*—Rough, somewhat scaly.

Internode length: 0.9 cm to 1.3 cm.

FOLIAGE

Leaf:

*Arrangement.*—Opposite, simple.

*Quantity.*—Approximately 12 to 16 per branch.

*Average length.*—Average range about 3.5 cm to 4.2 cm.

*Average width.*—Average range about 1.3 cm to 1.5 cm.

*Shape of blade.*—Oblong.

*Apex.*—Broad acute.

*Base.*—Attenuate.

*Margin.*—Entire.

*Aspect.*—Very slight undulation.

*Texture of top surface.*—Smooth.

*Texture of bottom surface.*—Smooth.

*Appearance of top surface.*—Glossy.

*Appearance of bottom surface.*—Matte.

*Color.*—

*Young foliage upper side.*—Near RHS Green 137A.

*Young foliage under side.*—Near RHS Green 137D.

*Mature foliage upper side.*—Near RHS Green 137A.

*Mature foliage under side.*—Near RHS Green 137C.

*Venation.*—Type: Pinnate. Venation color upper side: Mid-vein RHS 143C, lateral indistinguishable from blade. Venation color under side: Mid-vein RHS Yellow-Green 145C.

*Petiole.*—None.

FLOWER

Normal flowering period: Continuous to intermittent flower year round in Puerto Rico.

Inflorescence:

*Form.*—Somewhat flat simple umbel.

*Width of entire inflorescence.*—Average 6.5 cm.

*Height of entire inflorescence.*—Average 4.3 cm.

*Quantity of individual flowers in inflorescence.*—Average of 15.

Flower longevity on plant: Approximately 10 days.

Quantity of inflorescence per plant: Average 8 to 12.

Persistent or self-cleaning: Self-cleaning.

Bud:

*Shape.*—Linear tube, ending in a broader oblong apex.

*Length.*—Total, including tube 4.5 cm. 9 mm apex.

*Diameter.*—Tube 2 mm. Apex 4 mm.

*Color.*—Tube near RHS Yellow-Green 145A. Apex begins near RHS Yellow-Green 145C, turns near RHS White 155D closer to bud opening.

Individual flower:

*Form/type.*—Single, tubular flowers opening at the apex into 4 or 5 distinct petals.

*Apex diameter.*—2.2 cm.

*Tube diameter.*—2 mm.

*Length.*—Average 4.0 cm.

Petals: 4 or 5 petals fully fused into a long tubular symmetrical flower, outwardly flared at apex. Unfused petal section cruciform if 4, whorled if 5. Non-overlapping.

*Apex.*—Broad acute or rounded.

*Base.*—Fused.

*Texture.*—All surfaces glabrous.

*Unfused petal shape.*—Narrow ovate.

*Margin.*—Entire.

*Aspect.*—Unfused section strongly rolled downward.

*Color.*—

*Unfused section, immature.*—RHS White 155D, upper and lower surfaces.

*Tube immature outside surface.*—RHS Yellow-Green 145B.

*Tube immature inside surface.*—RHS Yellow-Green 145C.

*Upper section, mature.*—RHS White N155D, upper and lower surfaces.

*Tube mature outside surface.*—RHS Yellow-Green 145A.

*Tube mature inside surface.*—RHS Yellow-Green 145A.

Calyx: Reduced, formed of 5 fused sepals.

*Shape.*—Star-shaped.

*Length.*—5 mm.

*Width.*—6 mm.

*Sepal tip.*—Acute.

*Base.*—Fused

*Margin.*—Entire.

*Texture.*—Glabrous all surfaces.

*Color.*—Inner surface: Near Yellow-Green 144A. Outer surface: Near Yellow-Green 144A.

Peduncles:
*Length.*—Average 3 mm.
*Diameter.*—5 mm.
*Angle.*—Approximately 15° to the lateral branch.
*Strength.*—Strong.
*Texture.*—Scaly.
*Color.*—Near RHS Yellow-Green 144A.
Pedicels: Not present.
Fragrance: Moderately strong musky scent.

REPRODUCTIVE ORGANS

Stamens:
*Number.*—4 or 5.
*Length.*—Adnate to tube, separating at tube opening. 3 mm long separation. Colored near RHS Green-Yellow 145B.
Anthers:
*Length.*—Approximately 0.5 mm.
*Color.*—Near RHS Yellow 7A.
*Pollen.*—Color RHS Yellow 13A. Quantity: Scant.
Pistil:
*Number.*—1.
*Length.*—3.5 cm.
*Style.*—Length: 3.4 cm. Color: RHS Yellow-Green 145D.
*Stigma.*—Shape: 2 parted. Color: Near RHS Yellow-Green 147A. Ovary Color: Near RHS Yellow Green 145D.

OTHER CHARACTERISTICS

Seeds and fruits: Seed production not observed.
Disease/pest resistance: Neither resistance nor susceptibility to diseases or pests has been observed in this variety.
Temperature tolerance: Tolerates high temperatures to at least 40 degrees Celsius. Frost is not tolerated.
Drought tolerance: No drought tolerance.

What is claimed is:

1. A new and distinct cultivar of *Ixora* plant named 'Vista6' as herein illustrated and described.

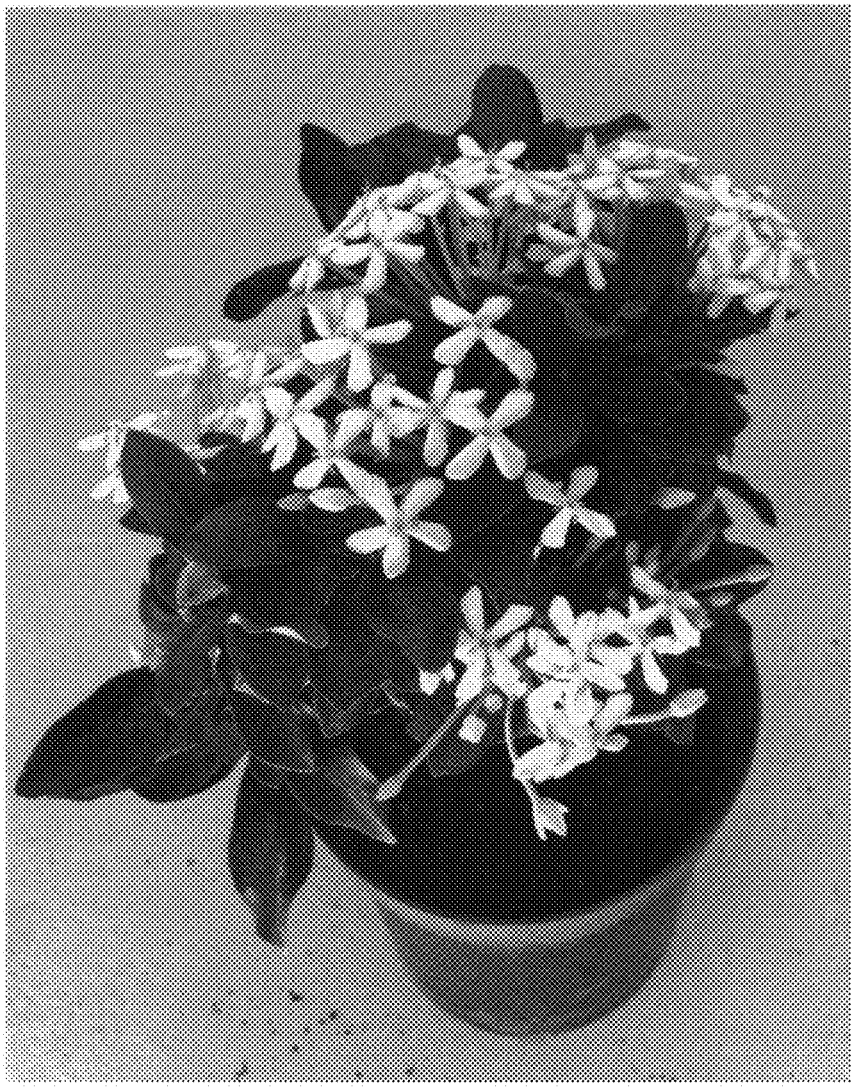

* * * * *